(12) United States Patent
Danielsson et al.

(10) Patent No.: US 7,342,233 B2
(45) Date of Patent: Mar. 11, 2008

(54) METHOD AND ARRANGEMENT RELATING TO X-RAY IMAGING

(75) Inventors: Mats Danielsson, Täby (SE); Mats Lundqvist, Täby (SE)

(73) Assignee: Sectra Mamea AB (SE)

( * ) Notice: Subject to any disclaimer, the term of this patent is extended or adjusted under 35 U.S.C. 154(b) by 0 days.

(21) Appl. No.: 11/282,547

(22) Filed: Nov. 18, 2005

(65) Prior Publication Data
US 2007/0114424 A1 May 24, 2007

(51) Int. Cl.
*G01T 1/24* (2006.01)
*H05G 1/64* (2006.01)
(52) U.S. Cl. ............... 250/370.09; 378/98.9; 378/98.11; 378/98.12
(58) Field of Classification Search ......... 250/370.09; 378/98.9, 98.11, 98.12
See application file for complete search history.

(56) References Cited

U.S. PATENT DOCUMENTS

| | | | | |
|---|---|---|---|---|
| 4,078,178 A | * | 3/1978 | Lowes | ............ 250/336.1 |
| 5,665,969 A | | 9/1997 | Beusch | |
| 5,847,398 A | | 12/1998 | Shahar et al. | |
| 2002/0196899 A1 | * | 12/2002 | Karellas | ............ 378/98.8 |

FOREIGN PATENT DOCUMENTS

| | | |
|---|---|---|
| EP | 00270761 | 6/1988 |
| WO | WO-01/27656 | 4/2001 |
| WO | WO-2004091405 | 10/2004 |
| WO | WO-2005/008286 | 1/2005 |

OTHER PUBLICATIONS

Norlin et al., "Energy Dependence in Dental Imaging with Medipx2", Nuclear Instruments & Methods in Physics Research, A 546 (2005) 19-23.
Johns et al., "Photon-Counting Detectors for Digital Radiography and X-Ray Computed Tomography", Optoelectronics, Photonics, and Imaging, SPIE TD01, (2002), 367-369.

* cited by examiner

*Primary Examiner*—David Porta
*Assistant Examiner*—Mark R Gaworecki
(74) *Attorney, Agent, or Firm*—Lerner, David, Littenberg, Krumholz & Mentlik, LLP

(57) ABSTRACT

An X-ray apparatus is provided for acquisition of images containing spectral information. An X-ray source and a collimator having multiple slits are operable together with a set of line detectors, the line detectors including linear arrays of photon counting channels. Each of the channels includes a photon conversion channel element which is operable to convert photons to electric pulses. A plurality of pulse counters are operable to count pulses in a plurality of different ranges of pulse strength, where the strength of a pulse depends on the energy of the photon. Further, an arrangement is included for an energy subtracting operation.

47 Claims, 6 Drawing Sheets

US 7,342,233 B2

METHOD AND ARRANGEMENT RELATING TO X-RAY IMAGING

TECHNICAL FIELD OF THE INVENTION

The present invention relates to a method and arrangement in x-ray imaging, in particular dual energy, contrast agents, photon counting detectors, and multi-slit scanners for mammography.

BACKGROUND OF THE INVENTION

The tissue around a typical cancer tumor is characterized by angiogenesis, which is a growth of nearby blood vessels supplying the growing tumor. Most likely, the tumor contains a lot more blood than healthy tissue. A widely used method of detection is to inject contrast agents and acquire images, either using x-ray imaging or magnetic resonance imaging (MRI). For x-ray imaging, the most widely used contrast agents are based on iodine, which attenuate x-rays more than normal tissue. High concentrations of a contrast agent make the tumor appear like a cloud in x-ray images, but unfortunately the cloud is super-imposed with anatomical structures, which may be strong enough to obscure the tumor. In addition, the amount of injected contrast agents should be kept at moderate levels, since they may cause allergic reactions and kidney failure. According to prior art, image subtraction is a widely used method to remove super-imposed tissue from the images, and obtain a resultant image where only the contrast agent appears. One method is temporal subtraction, where images are acquired before and after injection of contrast agents, and pre-contrast images are subtracted from post-contrast images, whereby all super-imposed structure is removed and only contrast agents remain. One problem of temporal subtraction is motion artifacts, which prevents the method from being used in cardiac imaging, and even breast imaging.

Another method is energy subtraction, where two or more images are acquired using different x-ray spectrum. Typically two images are acquired, based on spectral energies of low and high photon energies. Proper subtraction of high and low energy images cancels out most human tissue, and iodine contrast remains. The method is made possible thanks to the attenuation of iodine that has substantially different spectral curve, related to the electron energies in the K-edge of the iodine atom. The simplest method of achieving energy subtraction is to acquire two images in rapid succession, and in between change the voltage of the x-ray tube.

EP00270761A2 discloses a multi-layer flat-panel detector where photons are absorbed at different depth, depending on energy. The object is to perform energy subtraction, using a single exposure. There are, however, reasons to believe that a cost-effective production method still remains to be invented.

Figure 1:
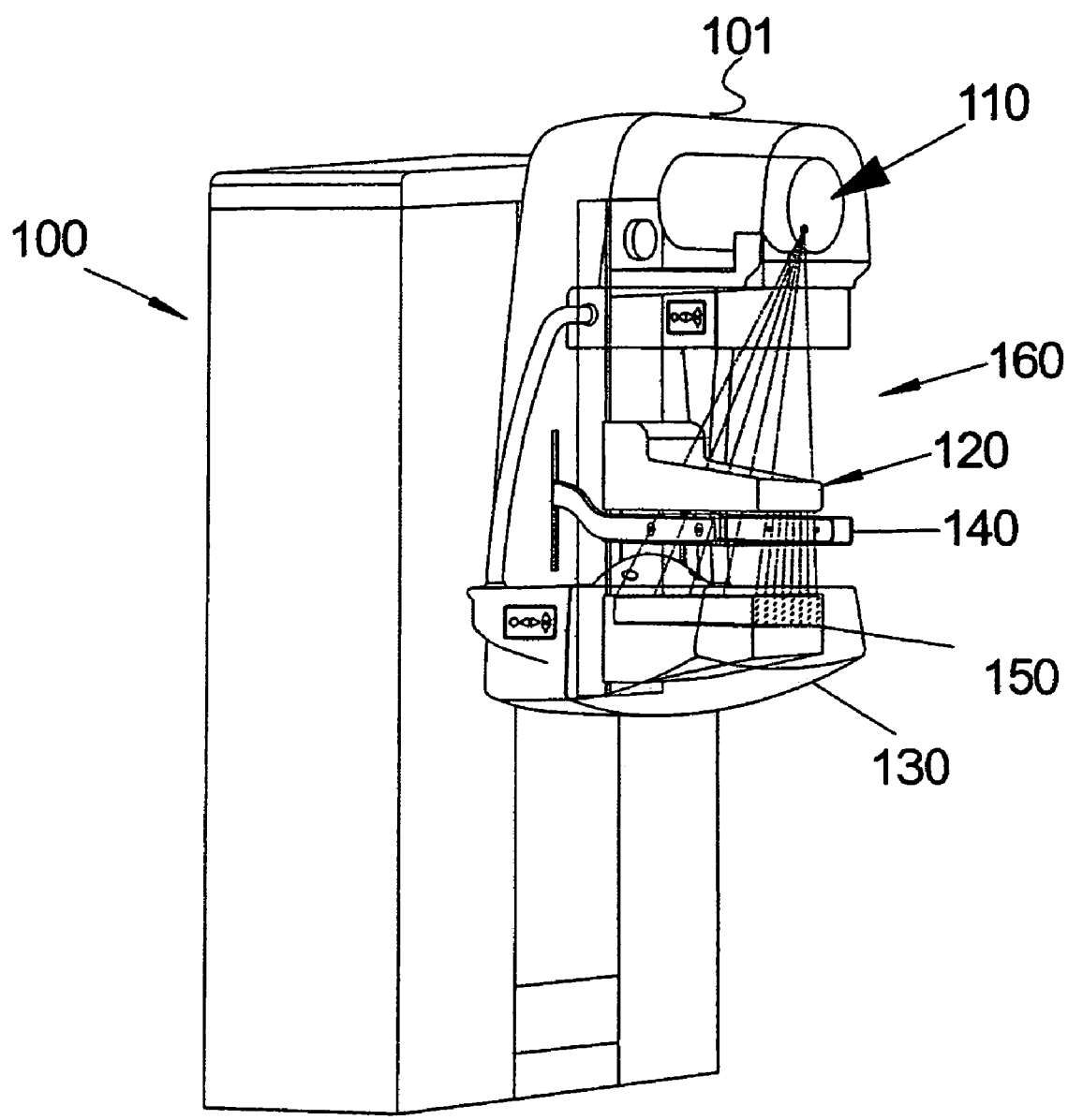
Figure 2:
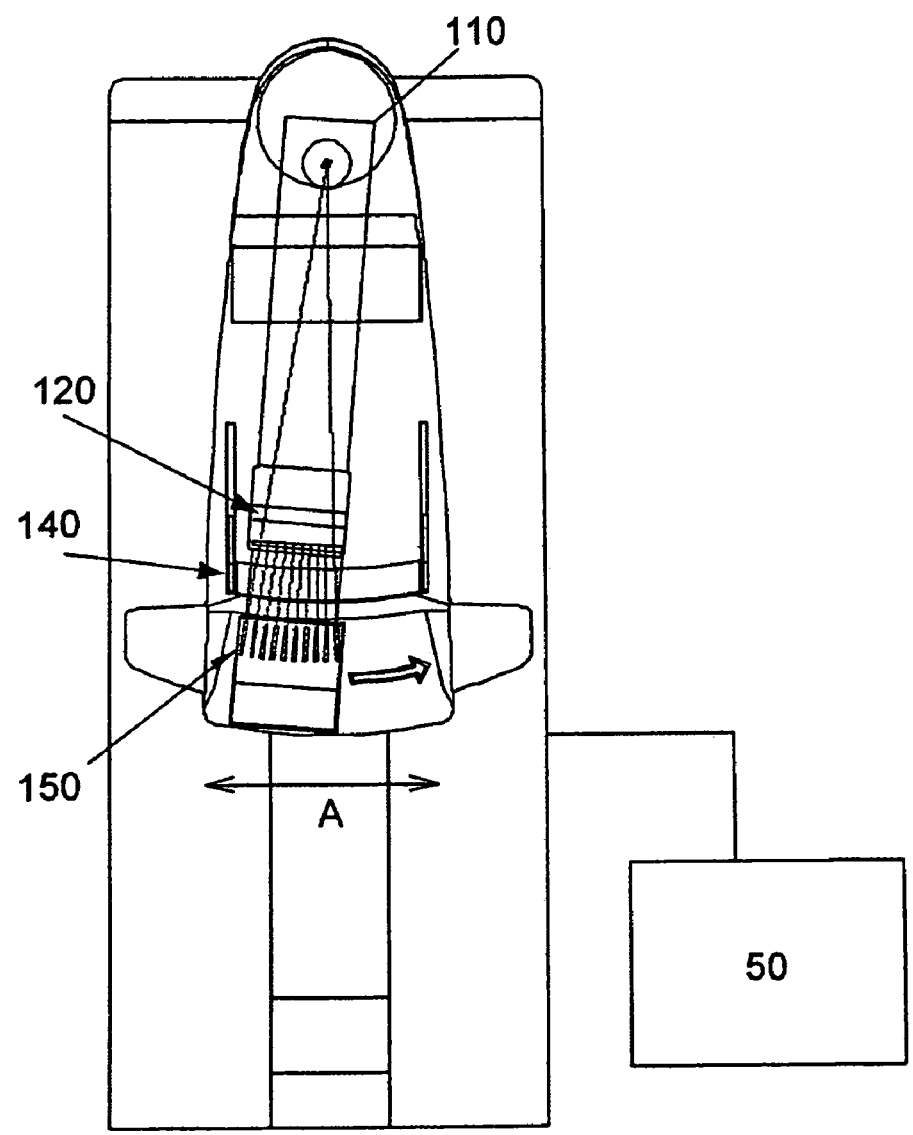
Figure 3:
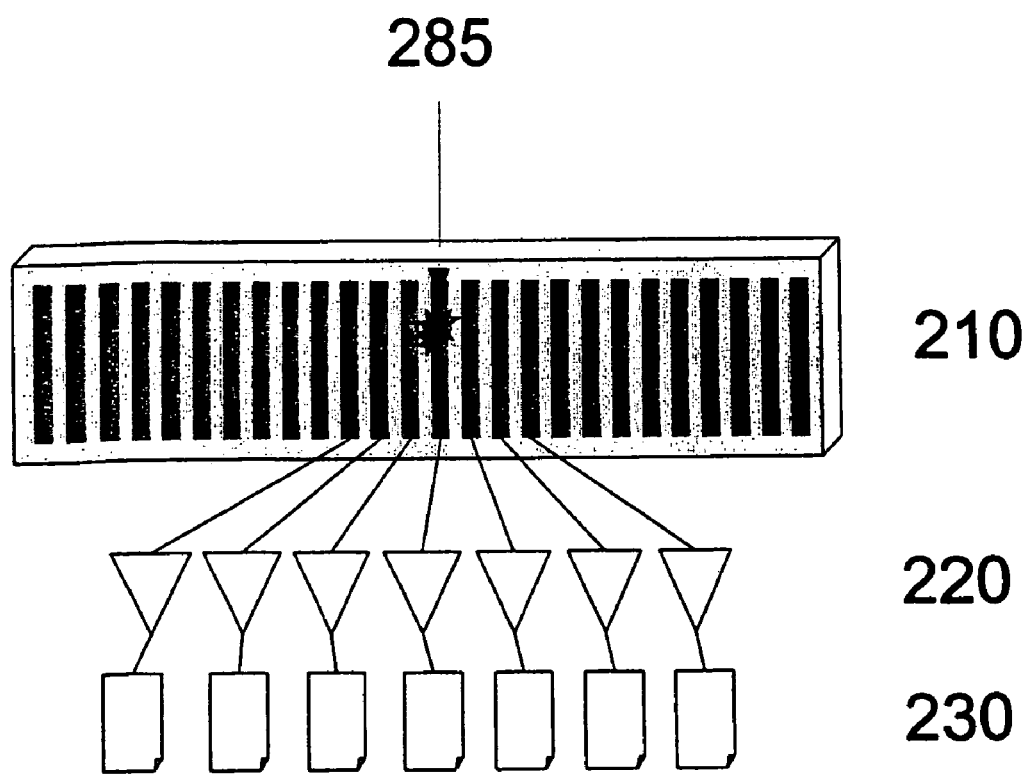

FIGS. 1 and 2 show prior art of a multi-slit x-ray scanner for acquisition of conventional x-ray mammograms without dual energy. The patient is irradiated by a bundle of thin, x-ray beams, each of which is detected by a corresponding line detector. Each beam has a rectangular cross-section, typically 4 centimeters wide and 50 micrometers across. The narrow beams are created by letting the x-rays pass through a collimator 120, which is a metal plate with several narrow linear apertures, referred to as slits. For each slit, there is one corresponding line detector. FIG. 3 illustrates a schematic line detector according to prior art. For visibility, only a few channels are drawn. Each line detector comprises a silicon array of photon conversion channel elements 210 and a corresponding array of pulse-counting circuits 230. Each photon conversion channel element has a width equal to the pixel size, which is 50 micrometers. Each photon conversion channel element converts photons to electric pulses, which are counted in a corresponding pulse counter. There is a strip on the surface of each photon conversion channel element. A strip is a layer on top of the semiconductor, which is connected by a small bond thread to an integrated circuit, comprising pre-amplifiers and pulse counters. The line detectors, the collimator and the x-ray source form an entity that is moveable by a scan motion. During irradiation by the x-ray source, the line detectors are moved relative the image area, whereby the set of line detectors acquire a set of overlapping part images. A resultant image is computed as the average of all overlapping part images. In FIGS. 1-2, the line detectors are mounted in a detector assembly 150. The breast to be irradiated is compressed using a compression plate 140. Among the advantages of multi-slit scanning are outstanding scatter rejection, low dose and photon counting.

WO04091405A1 discloses a multi-slit scanner where collimator slits are equipped with individual moveable filters. Thus, one exposure is enough to irradiate the imaged object with beams of different spectra, and perform dual energy examination. U.S. Ser. No. 05/665,969 discloses an x-ray detector and an x-ray apparatus, where photon energy is measured, and data is weighted depending on importance. Low energetic photons are given higher weight than high energetic photons, since low energy photons are more important. Each photon is absorbed in photon conversion channel element, where it is converted to an electric pulse and the photon energy is measured from the pulse strength. Several solutions are revealed, in particular a system with a limited number of energy levels and photons being accumulated using a weighted sum. There are individual weights at each level of energy. Neither negative weights nor energy subtraction is mentioned.

A spectral analyzing detector for computed tomography is disclosed in "Photon-Counting Detectors for Digital Radiography and X-Ray Computed Tomography", by Paul C. Johns, Jacques Dubeau, David G. Gobbi, Mei Li, and Madhu S. Dixit, Optoelectronics, Photonics, and Imaging, SPIE TD01, pages 367-369 (2002). The disclosed detector is a photon-counting gas micro-strip detector for computed tomography (CT), which measures the energy of each individual photon, based on the amount of electrical charge released when each photon hits the gas. Several applications are mentioned, for example corrections for beam hardening in artifacts in CT. Another mentioned application is image subtraction across K-edge energy level, to enhance iodine-based contrast agents.

SUMMARY OF THE INVENTION

The object of the invention is to provide a novel x-ray apparatus for acquisition of dual energy images, using a single exposure, and best possible image quality for a given dose. The invention is based on prior art of multi-slit scanning using a photon counting line detector.

The advantage relative to multi-layer flat panel detectors EP00270761A2 is ease of manufacture, and overall performance in conventional mammography imaging, i.e. imaging without subtraction.

The present invention also has advantage relative to variable slit filters, WO04091405A1. One advantage is fewer mechanical parts. Another advantage is that from each x-ray beam, the present invention produces two images, both high energetic and low energetic. Yet another advantage is full x-ray flux, in contrast to filtered x-ray beams, where known filters absorb a vast majority of photons in order to obtain a sufficiently different spectra. Furthermore, the present invention does not cause any scatter from filters in the collimator.

In contrast to previously mentioned spectral analyzing CT detector, the present invention is a full-fledged x-ray apparatus, detector technology and method for x-ray imaging, in particular mammography. The present invention comprises means and method for representing and accumulating statistics. In addition, the preferred embodiment can incorporate a solid state or semi-conductor detector, which has proven viable in a full-fledged x-ray imaging apparatus as shown in FIGS. 1-2. The present invention comprises circuits, which extend function of a complete mammography system, without impairing performance in any aspect.

One aspect of the present invention is a set of mechanisms for handling photons that are received between two channels, such that the charge is shared between two channels. Without such a mechanism, a low energy photon risks not be counted at all, and a high energy photon risks being counted as two low energy photons, i.e. in each of two neighboring channels. According to one aspect of the present invention, a mechanism prevents photons from being counted in more than one channel, and the photon energy is measured based on a sum of contributions from neighboring channels.

Another aspect of the present invention is a means and method for calibration.

Yet another aspect of the present invention is to produce multiple images from the same irradiation. Two images are enough to provide different views, such as subtraction for enhancing contrast agents and non-subtraction for view of tissue, like a normal x-ray image.

SHORT DESCRIPTION OF THE DRAWINGS

Figure 4:
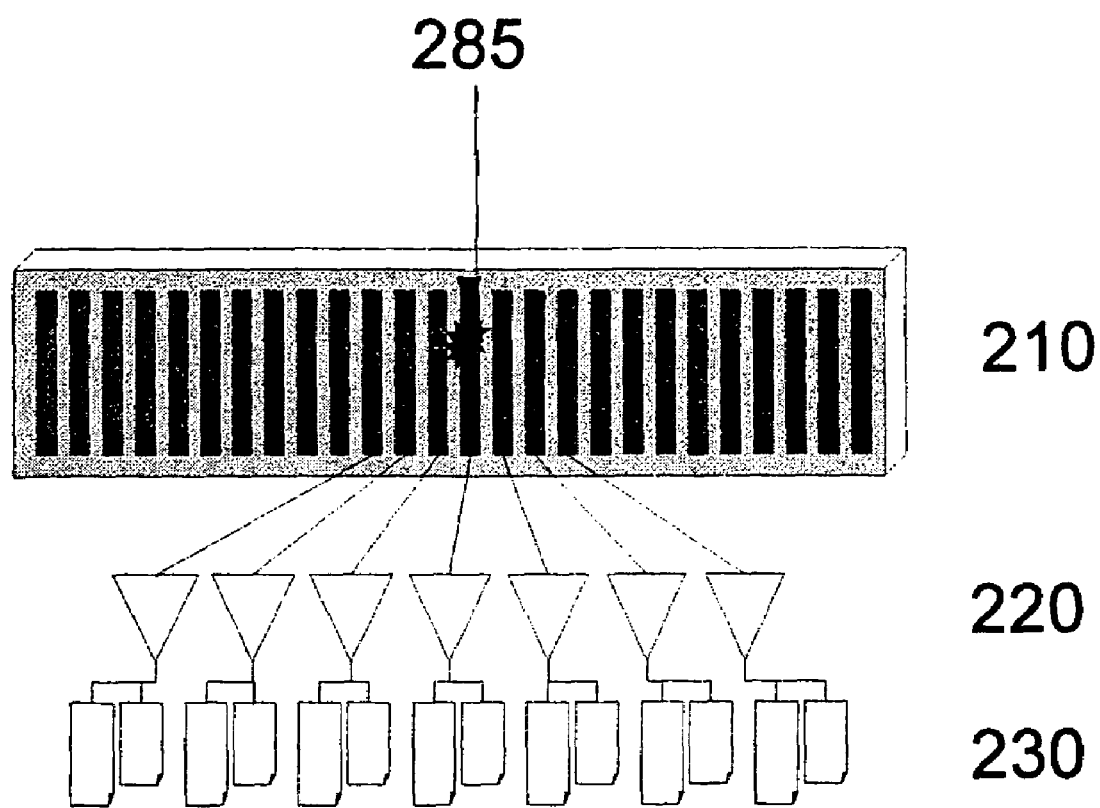
Figure 5:
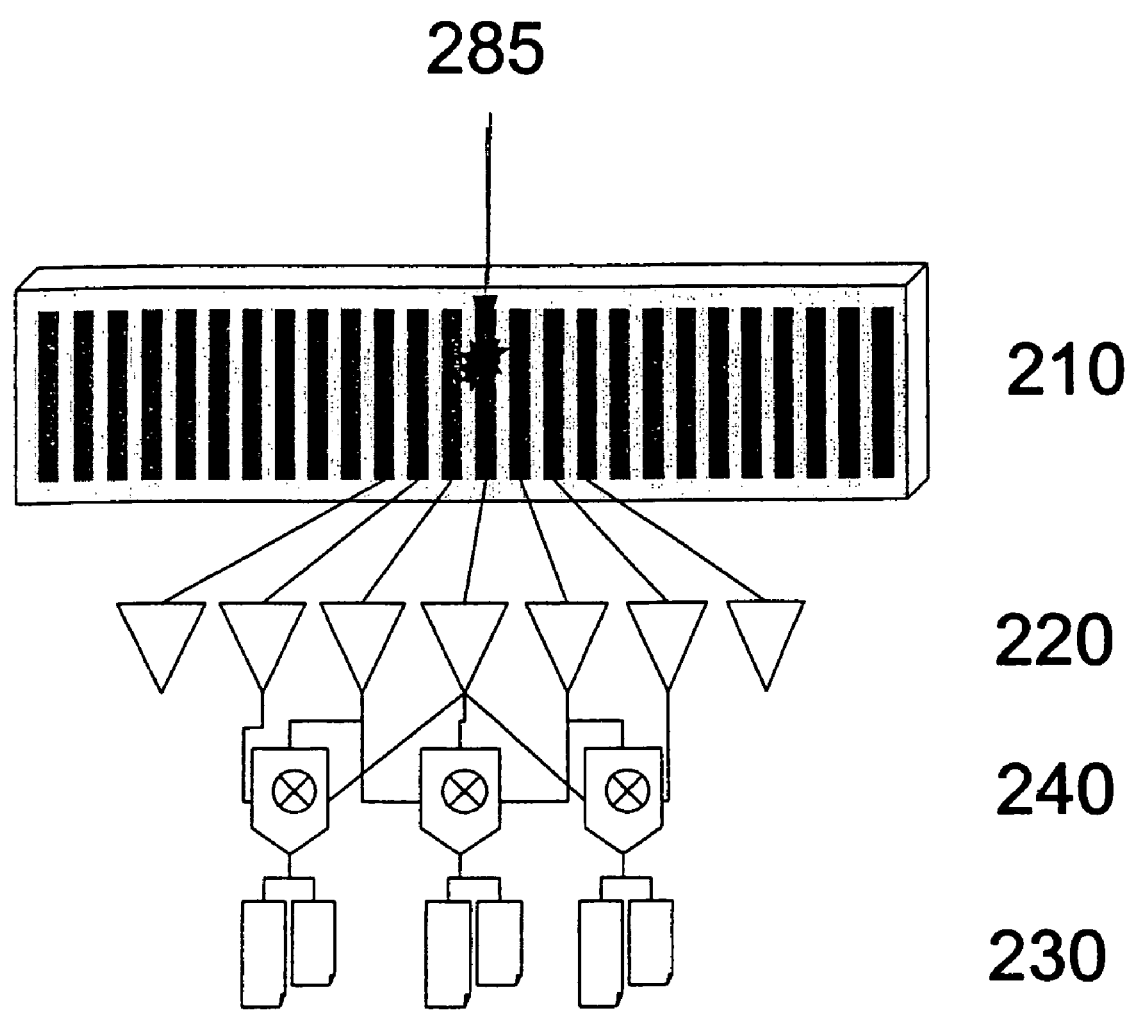
Figure 6:
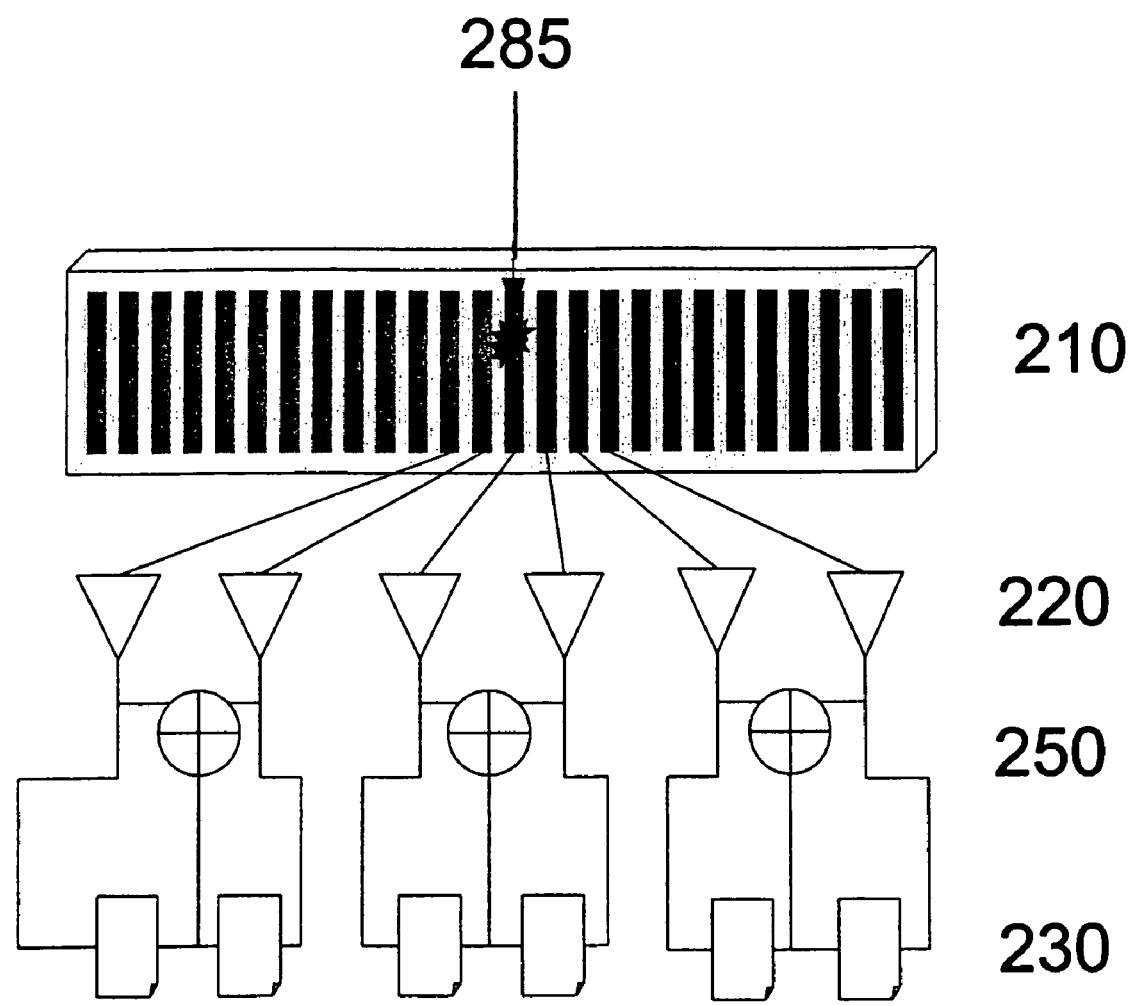

In the following the invention will be described in a non-limiting way with reference to enclosed drawings, in which:

FIGS. 1 and 2 are schematic illustrations of an x-ray arrangement according to the prior art, in particular a multi-slit scanner for mammography, FIG. 3 is a schematic illustration of an exemplary line detector, according to prior art, comprising a silicon array of photon conversion channel elements, and corresponding circuits, FIG. 4 is a schematic illustration of an exemplary line detector, of the present invention, equipped with dual counters, FIG. 5 is a schematic illustration of an exemplary line detector, of the present invention, equipped with dual counters and a circuit to handle photon signals shared by neighboring channels, and FIG. 6 is a schematic illustration of an exemplary line detector, of the present invention, where channels can possibly merge, whereby the apparatus is configurable to operate in two different modes.

DESCRIPTION OF THE EMBODIMENTS

In the following description same reference signs refer to same parts throughout the drawings.

The preferred embodiment is based on arrangement and mechanical parts of prior art. The mechanical arrangement may be identical to prior art of multi-slit scanners, in FIGS. 1-2, but underlying systems of electronics and software differ, according to the present invention.

A pulse counter is defined to be any scalar register, which is setup to increment or decrement its value for each received pulse. The step for increment or decrement may vary. The register representation may be integer, floating point or similar. In the most preferred embodiment, the counter is an integer value, which is incremented by a fixed step for each pulse, and never decremented, and the step is equal to one.

FIG. 4 illustrates a line detector according to one embodiment of the invention. The line detector comprises a silicon detector 210, which is an array of photon conversion channel elements, an array of pre-amplifiers 220 and an array of dual pulse counters. Alternatively, the line detector may also be described as an array of channels, wherein each channel comprises a photon conversion channel element of a silicon detector, a pre-amplifier and two pulse counters.

The silicon detector 210 is a semiconductor plate, arranged as an array of photon conversion channel elements, wherein each photon conversion channel element is essentially a wide PIN-diode. A constant bias voltage (not shown) is applied reverse, in order to obtain full depletion. Incident x-ray photons 285 hit silicon detector from the edge, and travel along the direction of the photon conversion channel elements, until being absorbed, whereby an electric pulse is triggered. In most cases, the pulse is limited to the photon conversion channel element where the photon was received, and the amplitude and the total charge depends on the energy of the absorbed photon.

A thin conductor leads the pulse from the photon conversion channel element, including strip, directly to a pre-amplifier 220. The pre-amplifiers 220 are arranged in an array of identical pre-amplifiers. There is one pre-amplifier for every photon conversion channel element. The pre-amplifiers may also include some non-linear filters and shapers for noise reduction and pulse refinement. According to the present invention, there are at least first and second pulse counters connected to each pre-amplifier. The two pulse counters are set up to be selective for different ranges of pulse strength. Most preferably, the first pulse counter has a low detection threshold and the second counter has a high detection threshold, whereby the first counter represents low energy photons and the second counter represents high energy photons. Preferably, the low energy counter comprises a mechanism to inhibit counting when the second counter detects a pulse, whereby no photon is counted in more than one counter per channel. An alternative to count inhibition is to let one counter count all pulses and later subtract the value of other counters.

The invention is not limited to disjoint parallel pulse counters. Without departing from the scope of the invention, the pulse counters may share many circuits. In the preferred embodiment two pulse counters share a common pulse gauge circuit and a low threshold decides whether the pulse is to be counted at all. A higher threshold decides which counter to increment its value. The paradigm can be generalized to any number of bins/counters, where a low threshold decides whether to register the pulse and another means assigns the pulse to one of several bins.

FIG. 5 illustrates a more sophisticated line detector than in FIG. 4, according to another embodiment of the invention. The line detector has been equipped with an array of anti-sharing circuits 240, which are connected essentially between the pre-amplifiers 220 and pulse counters 230. The anti-sharing circuits handle situation wherein a photon hits near a border between two photon conversion channel elements, and the electric pulse is shared. The effect is a smaller pulse in each of the channels. The anti-sharing circuit comprises two different mechanisms, namely anti-coincidence and neighbor integration. The anti-coincidence circuit prevents the shared pulse from being counted in more than one channel. Preferably, the anti-coincidence is implemented by comparison of one channel pulse to its neighbors, and inhibit counting when a neighbor registers a stronger pulse. The neighbor integration provides a better measurement of photon energy, by adding contributions from neighboring channels.

FIG. 6 illustrates a line detector of another embodiment where channels are able to merge pair-wise. The detector line is configurable to operate in either of two different modes, namely high resolution mode or dual energy mode. The high resolution mode is supposed to be equivalent to prior art, as shown in FIG. 3. The dual energy mode is supposed to be equivalent to FIG. 4. According to the embodiment in FIG. 6, the configurable components are the counters, which can be configured with respect to detection thresholds and which input signals to use. When configured to operate in high-resolution mode, the counters are configured to use equal detection threshold and input signal directly from the pre-amplifiers 220. When configured to operate in dual energy mode, the signals from the pre-amplifier are added pair-wise, by an array of summing junctions 250. The pulse counters are configured to receive signals from the summing junctions. Thus, every pair of channels is turned into one merged channel, comprising two pulse counters, each of which is configured to a different detection threshold, whereby one counts low energetic photons and the other counts high energetic photons.

The channel merger embodiment implies loss of resolution in dual energy mode, but spatial resolution tends to be less important in dual energy imaging than in normal imaging. The advantage of channel merging is a reduced amount of circuits and reduced power consumption. In addition, the approach simplifies electronics beyond the detector prior art of components that can be used. In particular, the dual energy requires no more bandwidth or memory buffers than components for prior art of multi-slit scanning. Furthermore, anti-sharing electronics become less critical, as half the photon conversion channel element borders can be ignored.

In a more elaborate embodiment, it is possible to merge channels that already have a plurality of counters. The advantage is to get an even higher number of counters for each channel, whereby the x-ray spectrum can be measured using more bins of photon energy. By merging channels, spectral resolution can be bought at the price of spatial resolution.

The embodiments in FIGS. 4-6 can also be described in an alternative view, wherein counters are classified or re-organized into a matrix. Each column corresponds to one channel and each row corresponds to one energy level.

In the preferred embodiment, the data from counters are read out during image acquisition and stored in a memory buffer. The readout is triggered at regular intervals of the scan motion, corresponding to the image pixel size. A first and a second image are constructed, according to prior art. The first image is constructed from data from those pulse counters that are tuned for low energetic photons. The second image is constructed from those pulse counters that are tuned for high energetic photons.

In other embodiments, images may be constructed from weighted sums or weighted differences of pulse counter values. A more general description is to use linear combinations of the counter values in a channel. Extraction of only one counter value is a special case of a linear combination, where all coefficients but one are zero. Thus, all preferred embodiments use linear combinations of counter values.

Preferably, image construction and image processing are based on the following set of operations: averaging of overlapping data from different line detectors, convolution, low pass filtering, sub-sampling, image pyramids and pixel-wise nonlinear transforms, such as logarithms. The system comprises software for producing linear combinations of the first and second image, whereby noise is reduced or human tissue is separated from contrast agents.

The preferred embodiment produces multiple images for every irradiation and data acquisition. The number of images is equal to the number of photon counters per channel. Linear combinations of the images can be displayed, in order to obtain different views. In one view, the level of subtraction may be optimized in order to fully separate out contrast agent and fully cancel out human tissue. In another view, subtraction may be replaced by weighted addition, in order to produce a normal x-ray image. Preferably, the different views should be displayed in the same position and the user should be able to switch between different views without flicker. The preferred embodiment comprises a mechanism for exporting a plurality of views to a general system for image storage and display, commonly known as picture archiving and communicating system (PACS).

In order to obtain high quality energy subtraction images, calibration of detection thresholds is necessary. The system should be calibrated such that the first pulse counter in one detector channel should have the same detection thresholds as the first pulse counter in all other channels. Similarly, the detection threshold of the second pulse counter should be equal for all channels. For a system with two counters per channel, it is particularly important to calibrate the thresholds that determine whether a photon is high energetic or low energetic. In addition, the optimal detection thresholds also depend on type of imaging. The primary application of dual energy subtraction is to separate iodine contrast agent from human tissue, using logarithms and then subtraction of high energy and low energy photons. In order to obtain best results, the threshold between low and high energy should be close to the K-edge electron energy of the iodine atom, which implies photon energies about 33 keV. The preferred algorithm of calibration is to irradiate the photon conversion channel elements with a known tube voltage, preferably close to 33 kv. The threshold is changed during irradiation, and a computer program finds the cut-off threshold, which is the lowest threshold at which no photons are counted as high energetic. Finally, the threshold may be adjusted by an offset, which is determined from empirical studies and depends on the difference between tube voltage and desired threshold of photon energy.

An alternative embodiment of calibration uses a calibration phantom containing a filter material, such as iodine. Preferably, the phantom contains elongated rectangular regions of different level of iodine, and those rectangles are elongated orthogonal to the scan direction, such that every channel in every detector line acquires images of different levels of iodine.

The invention is not limited to multi-slit scanners. Future development in semiconductor industry is expected to enable manufacture of commercially viable flat-panel detectors with photon-counting abilities. According to prior art of research, photon-counting flat-panel detectors have already been manufactured for research. The invention is applicable to any kind of image acquisition technology, including slot scanning and flat panel detectors.

In one particular embodiment of the present invention, the counters increment or decrement their values of different steps, and the step length depends on photon energy, as further disclosed in U.S. Ser. No. 05/665,969. The rules of number of increments for each type of pulse should be configurable depending on voltage of x-ray source, x-ray filters, thickness of imaged object and kind of contrast agent.

Image subtraction is a part of all preferred embodiments. The purpose of dual energy and energy subtraction is to cancel out structures of one spectrum, but keep structures of another spectrum. Preferably, the purpose of image subtraction is to cancel out human tissue, but not contrast agent. The preferred method is subtraction of high energy and low energy images. Before subtraction, logarithm is applied to the high energy and low energy images respectively. Without logarithm, the intensity, of the subtraction images would depend on the amount of super-imposed structure, such that the contrast agent would be less strong in areas where there is much super-imposed structure. Preferably, the logarithm is quasi-logarithm rather than a genuine logarithm, since the logarithm of zero cannot be computed. After logarithm, each image is multiplied by scalar. Different scalar multipliers are applied on the images, and the scalars are chosen such that human tissue cancels out in the subtraction. The scalar multiplier should be calibrated, computed automatically or selected by the user, in order to cancel out human tissue. In some cases, it is desired to cancel out all human tissue.

There are many variations of subtraction. For example, division is equivalent to subtraction in logarithm domain. In addition, the logarithm may be approximated by many non-linear curves. The subtraction may be approximated by a look-up-table of two variables.

Therefore, the invention is generalized to any energy subtracting operation. The word energy subtracting operation refers to any operation where photons contribute to the result with opposite signs, depending on energy level. For example, when subtracting a low energy image from a high energy image, the result gets greater (i.e. more positive or less negative) for every high energy photon that hits the detector, but the result gets smaller for every low energy photon. Division is also an energy subtracting operation. From a mathematical point of view, partial derivatives can tell whether a system comprises an energy subtracting operation. The method is to mathematically derive partial derivatives of a pixel value, with respect to the number of received photons of different energy levels. The system comprises an energy subtracting operation if one derivative is negative and another derivative is positive. Preferably, the test should be applied on raw image, or raw signals without any extensive image processing, such as thickness equalization or normalization of average.

The energy subtracting operation may be applied anywhere in the chain from counters to displayed image, including the possibility that counters may decrement values for photons of some energy. The present invention is not limited to any particular position of energy subtracting operation, but preferably, the energy subtraction operation is applied after merging signals from different detector lines, but before image display.

The above mentioned and described embodiments are only given as examples and should not be limiting to the present invention. Other solutions, uses, objectives, and functions within the scope of the invention as claimed in the below described patent claims should be apparent for the person skilled in the art.

What we claim is:

1. An x-ray apparatus for acquisition of images containing spectral information, comprising:
   a) an x-ray source operable to output a plurality of x-ray photons;
   b) a multi-slit collimator having a plurality of openings operable to direct the x-ray photons into a plurality of beams;
   a set of line detectors each aligned with one of the openings to receive the x-ray photons of one of the beams each of said line detectors being a linear array of photon counting channels, each of said channels comprising a photon conversion channel element being operatively arranged to directly convert each received x-ray photon to an electric pulse, said pulse having a strength depending on the energy of the x-ray photon converted thereto;
   c) a plurality of pulse counters including first counters operable to count said pulses which have a first range of pulse strength and second counters operable to count said pulses which have a second range of pulse strength lower than said first range; and
   d) an arrangement for energy subtracting operation.

2. The x-ray apparatus according to claim 1, being arranged to compute an image according to a function designed such that an additional received photon either increases or decreases a pixel value of said image, depending on the energy of said additional photon.

3. The x-ray apparatus according to claim 2, further comprising an arrangement for producing an additional image without an additional irradiation, said arrangement being arranged to produce said additional image without applying said energy subtracting operation.

4. The x-ray apparatus according to claim 1, wherein said apparatus is intended for mammography.

5. The x-ray apparatus according to claim 1, further comprising an arrangement for handling information about contrast agent injected to a patient.

6. The x-ray apparatus according to claim 1, wherein said counters are arranged to increment or decrement in variable steps for each of said pulses, and said steps depend on properties of said pulses.

7. The x-ray apparatus according to claim 1, further comprising a means for neighbor integration of pulse strength, whereby said pulse counters receive contributions from two or more neighboring channels.

8. The x-ray apparatus according to claim 1, wherein at least one of said channels comprises an anti-coincidence mechanism, for preventing counting a photon when a neighbor channel receives a stronger pulse.

9. The x-ray apparatus according to claim 1, wherein said apparatus comprises an arrangement for variable spatial and spectral resolution, wherein each of said channels is configurable to merge with or split from neighboring channels.

10. The x-ray apparatus according to claim 1, wherein said photon conversion channel elements are essentially semiconductor PIN junctions, arranged as a linear array on a semiconductor plate.

11. The x-ray apparatus according to claim 1, further comprising an image generating arrangement, operatively arranged to generate an image based on pixel-wise contributions from essentially all of said channels in essentially all of said line detectors, wherein said pixel-wise contributions are linear combinations of values from one or several of said counters within the same channel, and moreover said linear combinations are variable.

12. The x-ray apparatus according to claim 11, further comprising an image generating arrangement, operatively arranged to generate at least two images, and said two images are based on data from the same exposure by said x-ray source, wherein said two images are different with respect to said linear combinations.

13. The x-ray apparatus according to claim 12, further comprising image display and a user interface for control of said energy subtracting operation.

14. The x-ray apparatus according to claim 1, further comprising a calibration tool for calibration of said ranges in said pulse counters, wherein said ranges are adjustable by parameters, and said calibration tool comprises a first means for performing irradiation by said x-ray source, a second means for receiving statistics from said counters, a third means for computing improved values of said parameters, and a fourth means for adjusting said parameters, wherein said third means is set up to compute said improved parameters at least partly based on desired ranges, said statistics from said counters and voltage to said x-ray source used by said first means.

15. The x-ray apparatus according to claim 14, further comprising at least one of a pre-defined phantom or filter locatable between said x-ray source and said line detectors during said irradiation, said third means being operable to compute said improved parameters partly based on known physical properties of said at least one of a phantom or filter.

16. A method of producing an image containing spectral information, comprising the steps of:
irradiation by an x-ray source an array of channels of photon conversion channel elements, whereby each photon conversion channel element converts photons to electric pulses,
counting said pulses in a plurality of parallel counters per channel,
reading out values from said counters from essentially all of said channels,
constructing an image from said values, and
outputting said image,
wherein the strength of said pulses depends on the energy of said photons, and at least two of said counters per channel count pulses in different ranges of said strength, and applying an energy subtracting operation, said output being either image display or image export to another system.

17. The method according to claim 16, wherein different x-ray photons contribute to pixel values of said image, and an additional received x-ray photon either increases or decreases a pixel value, depending on the energy of said x-ray photon.

18. The method according to claim 17, wherein said method is applied in a multi-slit scanner.

19. The method according to claim 17 or claim 18, wherein said counters increment or decrement by variable steps, depending on properties of said pulses.

20. The method according to claim 17 or claim 18, wherein a body part of a patient is irradiated and contrast agent is injected to said patient prior to said irradiation.

21. The method according to claim 20, wherein the application is mammography and said body part is a breast.

22. The method according to claim 17, further comprising a method of calibration of said ranges of pulse strength, wherein said method comprises the steps of irradiating said line detectors with a reference spectrum of photon energies, acquisition of statistics of counts for each counter in each channel and adjusting detection thresholds of said pulse counters.

23. The method according to claim 22, wherein said reference spectrum is obtained by setting a voltage of said x-ray source, whereby the maximum energy of x-ray photons emitted from said x-ray source is near the desired level of threshold to calibrate.

24. The method according to claim 22, wherein said reference spectrum is obtained by inserting at least one of a filter or phantom, the voltage of said x-ray source is essentially at a level usable for acquisition of an image, and said at least one of a filter or phantom contains a material of a type usable as a contrast agent present within a patient during acquisition of the image.

25. The method according to claim 16, wherein an additional image is produced without an additional irradiation, wherein said energy subtracting operation is either adjusted or not applied.

26. An x-ray apparatus for acquisition of images and energy subtraction, comprising:
an x-ray source,
a multi-slit collimator,
a set of line detectors, each of said line detectors comprises a photon conversion volume for conversion of photons of different energies to electric pulses of different strengths,
an arrangement for image construction,
an arrangement for energy subtraction,
a number of pulse counters, comprising a plurality of rows and a plurality of columns, each row corresponding to a unique range of photon energy and each column being connected to a unique region in said photon conversion volume, and said counter in each of said columns and each of said rows being operatively arranged to count photons from said region corresponding to said column and in said range corresponding to said row.

27. The x-ray apparatus according to claim 26, wherein said number of pulse counters is a matrix, which is an imagined, virtual or logical order, which is independent of physical layout or topology.

28. The x-ray apparatus according to claim 27, wherein essentially each of said columns is equipped with an anti-coincidence mechanism, which is set up to prevent counting a photon when a stronger pulse is received in a column corresponding to an adjacent region of said photon conversion volume.

29. The x-ray apparatus according to claim 27, wherein essentially each of said columns is equipped with an arrangement for neighbor integration, whereby said pulse counters receive contributions from two or more neighboring regions of said photon conversion volume.

30. The x-ray apparatus according to claim 27, wherein said counters are set up to increment or decrement variable steps for each of said pulses, wherein said step depends on properties of said pulses.

31. The x-ray apparatus according to claim 27, further comprising means for handling information about contrast agent injected to a patient.

32. An x-ray apparatus according to claim 26, wherein said apparatus further comprises an arrangement for producing an additional image without an additional irradiation, and said arrangement being arranged to produce said additional image without applying said energy subtracting operation.

33. An x-ray apparatus for producing an image, comprising an array of photon counting channels, and an arrangement for image construction operable to perform an energy subtracting operation when constructing an image, and each of said channels comprises a photon conversion channel element, and a plurality of pulse counters including first counters and second counters, wherein said photon conversion channel element is characterized by conversion of x-ray photons to electric pulses whose strength depends on the energy of said x-ray photons, and furthermore said counters are directly or indirectly connected to said photon conversion channel element, said first counters being operable to count said pulses which have a first range of pulse strength and said second counters being operable to count said pulses which have a second range of pulse strength lower than said first range.

34. The x-ray apparatus according to claim 33, wherein said arrangement for image construction is arranged to compute an image according to a function, and said function is designed such that an additional received x-ray photon either increases or decreases a pixel value of said image, depending on the energy of said additional x-ray photon.

35. The x-ray apparatus according to claim 34, wherein the pixel size of said image is essentially equal to the size along one dimension of said photon conversion channel element.

36. The x-ray apparatus according to claim 34, wherein said apparatus is intended for mammography.

37. The x-ray apparatus according to claim 34, further comprising means for handling information about contrast agent injected to a patient.

38. The x-ray apparatus according to claim 34, wherein said counters are set up to increment or decrement variable steps for each of said pulses, and said steps depend on properties of said pulses.

39. The x-ray apparatus according to claim 34, further comprising an arrangement for neighbor integration of pulse strength, whereby said pulse counters are set up to make decisions based on contributions from at least two neighboring channels.

40. The x-ray apparatus according to claim 34, wherein at least one of said channels comprises an anti-coincidence mechanism, which is set up to prevent counting a photon when a neighbor channel receives a stronger pulse.

41. The x-ray apparatus according to claim 34, wherein said photon conversion channel elements are essentially semiconductor PIN junctions, arranged as an array on a semiconductor plate.

42. The x-ray apparatus according to claim 34, further comprising a calibration tool intended for calibration of said ranges of said pulse counters, wherein said ranges are adjustable by parameters, and said calibration tool comprises a first arrangement for performing irradiation by said x-ray source, a second arrangement for receiving statistics from said counters, a third arrangement for computing improved values of said parameters, and a fourth arrangement for adjusting said parameters, wherein said third arrangement is set up to compute said improved parameters at least partly based on desired ranges, said statistics from said counters and voltage to said x-ray source used by said first arrangement.

43. The x-ray apparatus according to claim 42, further comprising a pre-defined phantom or filter, intended to be located between said x-ray source and said line detectors during said irradiation, and said third arrangement being arrangement to compute parameters partly based on known physical properties of said phantom or filter.

44. The x-ray apparatus according to claim 33, wherein said apparatus further comprises an arrangement for producing an additional image without an additional irradiation, said arrangement being operable to produce said additional image without applying said energy subtracting operation.

45. A detector assembly for use in an x-ray apparatus comprising a set of line detectors, each of said line detectors being a linear array of photon counting channels, each of said channels comprising a photon conversion channel element being operatively arranged to convert an x-ray photon incident thereon to an electric pulse, said pulse having a strength depending on the energy of said x-ray photon, and having a connection arrangement for connection to a plurality of pulse counters, said first counters being operatively arranged to count said pulses which have a first range of pulse strength and said second counters being operatively arranged to count said pulses which have a second range of pulse strength lower than said first range.

46. A pulse counter arrangement for use in an x-ray apparatus, comprising a plurality of rows and a plurality of columns, each row corresponding to a unique range of photon energy and each column connectable to a region in a photon conversion volume, said counter in each of said columns and each of said rows being operatively arranged to count photons from said region corresponding to said column and in said range corresponding to said row.

47. The pulse counter according to claim 46, being arranged as a matrix.

* * * * *

UNITED STATES PATENT AND TRADEMARK OFFICE
CERTIFICATE OF CORRECTION

PATENT NO. : 7,342,233 B2  Page 1 of 1
APPLICATION NO. : 11/282547
DATED : March 11, 2008
INVENTOR(S) : Mats Danielsson and Mats Lundqvist It is certified that error appears in the above-identified patent and that said Letters Patent is hereby corrected as shown below:

Column 3, lines 16, 17, after "circuits" insert --,--.
Column 8, line 11, after "beams" insert --,--.
Column 8, line 39, "to" should read --into--.
Column 9, line 30, after "source" insert --of--.
Column 9, line 58, "to" should read --into--.
Column 10, lines 21, 22 "comprises" should read --comprising--.
Column 10, line 56 "to" should read --into--.
Column 10, line 57, "An" should read --The--.
Column 11, line 26, "to" should read --into--.

Signed and Sealed this

Twenty-eighth Day of April, 2009

JOHN DOLL
*Acting Director of the United States Patent and Trademark Office*